United States Patent
Takebe et al.

[11] Patent Number: 5,478,871
[45] Date of Patent: Dec. 26, 1995

[54] POLYHYDRIC PHENOL FROM NAPHTHALDEHYDE AND EPOXY RESIN OBTAINED USING THE SAME

[75] Inventors: Kazuo Takebe; Takashi Morimoto; Yutaka Shiomi; Yasuhide Sugiyama, all of Tsukuba; Shigeki Naitoh, Tokyo; Noriaki Saito; Shuichi Kanagawa, both of Tsukuba; Kunimasa Kamio, Toride, all of Japan

[73] Assignee: Sumitomo Chemical Company, Limited, Osaka, Japan

[21] Appl. No.: 287,251

[22] Filed: Aug. 8, 1994

Related U.S. Application Data

[63] Continuation of Ser. No. 957,890, Oct. 8, 1992.

[30] Foreign Application Priority Data

Oct. 11, 1991 [JP] Japan ................. 3-263658
May 22, 1992 [JP] Japan ................. 4-130600

[51] Int. Cl.$^6$ ............................................. C08L 63/00
[52] U.S. Cl. .................... 523/443; 523/457; 523/458; 523/459; 523/466; 525/481; 525/482; 525/484; 525/486; 528/97; 427/386; 264/572
[58] Field of Search ........................ 427/386; 523/443, 523/466, 457, 458, 459; 525/481, 486, 482, 484; 528/97; 264/572

[56] References Cited

U.S. PATENT DOCUMENTS 4,960,634 10/1990 Boyko et al. ................. 428/220

FOREIGN PATENT DOCUMENTS 0038689 10/1981 European Pat. Off. .
0414537 2/1991 European Pat. Off. .
62-25116 2/1987 Japan .
62-167318 7/1987 Japan .
1271415 4/1988 Japan .
3163126 7/1991 Japan .

Primary Examiner—Frederick Krass
Attorney, Agent, or Firm—Cushman Darby & Cushman

[57] ABSTRACT

The present invention provides polyhydric phenols which are starting materials for glycidyl ether compounds which can provide cured products having low moisture absorption, high heat resistance and improved crack resistance and can be used for encapsulating semiconductor devices. The polyhydric phenols are represented by the following formula:

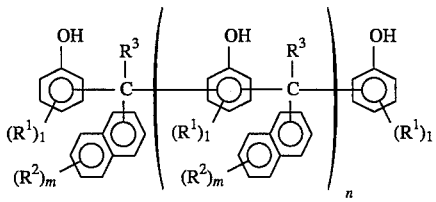

wherein $R^1$ independently represents a halogen atom, an alkyl or cycloalkyl group of 1–9 carbon atoms, an alkoxy group of 4 or less carbon atoms or an aryl group and $R^1$ may be identical or different when l is 2 or more, $R^2$ independently represents a halogen atom, an alkoxy group of 4 or less carbon atoms or an alkyl group of 6 or less carbon atoms and $R^2$ may be identical or different when m is 2 or more, $R^3$ independently represents a hydrogen atom or an alkyl group of 6 or less carbon atoms, the average recurring unit number n is 0–10, l is 0–4 and m is 0–7, and can be contained as a curing agent in an epoxy resin composition which is used not only for giving cured products but also for encapsulating semiconductor devices.

9 Claims, No Drawings

POLYHYDRIC PHENOL FROM NAPHTHALDEHYDE AND EPOXY RESIN OBTAINED USING THE SAME

This is a continuation of Application No. 07/957,890, filed Oct. 8, 1992.

BACKGROUND OF THE INVENTION

The present invention relates to polyhydric phenols and epoxy resins obtained using them as starting materials. The epoxy resins of the present invention are useful especially as encapsulants for electronic parts.

Recently, transfer molding of epoxy resin compositions which are economically advantageous has been carried out for encapsulation of semiconductors such as LSI, IC and transistors. Especially, surface mounting has been carried out for LSI and direct dipping in bath of solder has often been conducted. In this case, since encapsulants are exposed to high temperatures of higher than 200° C., water absorbed and contained therein expands to cause cracking.

Therefore, epoxy resin encapsulants are required to be low in moisture absorption and have resistance to cracking and at present, glycidyl ethers of o-cresol novolak are mainly used. Further, encapsulants comprising glycidyl ethers of tetramethylbiphenol were developed to improve the moisture absorption. [Japanese Patent Kokai (Laid-Open) No. Hei 1-283241]

Moreover, glycidyl ethers of condensates of α-naphthol with aldehydes have been known as epoxy resins low in water absorption and excellent in heat resistance. Japanese Patent Kokai No. Sho 62-25116).

Encapsulants mainly composed of glycidyl ethers of o-cresol novolak are excellent in heat resistance and are somehow superior in balancing of heat resistance and low moisture absorption, but they are not necessarily satisfactory in the use which requires low moisture absorption of higher level as mentioned above and improvement has been demanded.

The glycidyl ethers of tetramethylbiphenol are superior in low moisture absorption, but are not necessarily enough in heat resistance. Therefore, they are limited in their use as encapsulants.

Furthermore, glycidyl ethers of condensates of α-naphthol with aldehydes are low in moisture absorption, but high in melt viscosity even in the case of low polymerization degree and inferior in operability and besides, insufficient in heat resistance.

SUMMARY OF THE INVENTION

An object of the present invention is to provide polyhydric phenols which are starting materials for glycidyl ether compounds which give cured products lower in moisture absorption, improved in crack resistance and high in heat resistance, the glycidyl ether compounds and compositions thereof.

Another object of the present invention is to provide epoxy resin compositions containing a specific polyhydric phenol curing agent which gives the cured products as mentioned above and the present invention further provides the use of the compositions.

That is, (1) the present invention provides a polyhydric phenol represented by the following formula

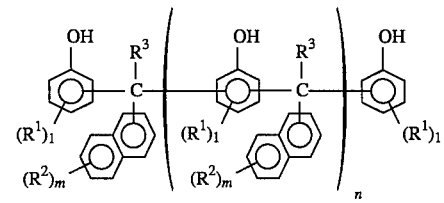

(1)

wherein $R^1$(s) each independently represents a halogen atom, an alkyl or cycloalkyl group of 1–9 carbon atoms, an alkoxy group of 4 or less carbon atoms or an aryl group, with a proviso that $R^1$(s) may be identical or different when l is 2 or more, $R^2$(s) each independently represents a halogen atom, an alkoxy group of 4 or less carbon atoms or an alkyl group of 6 or less carbon atoms, with a proviso that $R^2$(s) may be identical or different when m is 2 or more, $R^3$(s) each independently represents a hydrogen atom or an alkyl group of 6 or less carbon atoms and may be identical or different, the average recurring unit number n is 0–10, l is 0–4 and m is 0–7.

(2) The present invention also provides a glycidyl ether compound represented by the following formula (2):

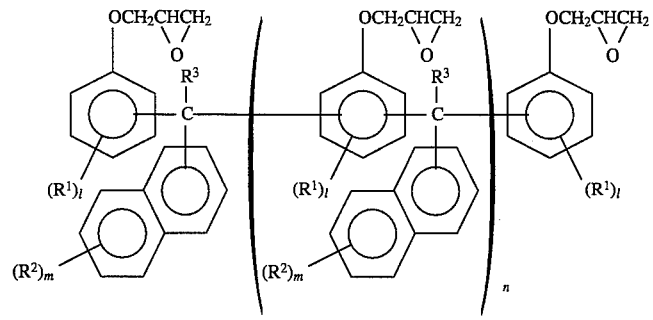

(2)

wherein the symbols have the same meanings as defined above.

(3) The present invention further provides an epoxy resin composition comprising the glycidyl ether compound mentioned in the above (2) and a curing agent.

(4) The present invention additionally provides an epoxy resin composition which contains as main components (a) an epoxy resin having at least two epoxy groups in the molecule and (b) a polyhydric phenol represented by the formula (1).

(5) The present invention further provides a process for using the epoxy resin composition mentioned in the above (3) or (4) for encapsulating a semiconductor device.

DESCRIPTION OF THE PREFERRED EMBODIMENTS

The first invention relates to polyhydric phenols which are starting materials for glycidyl compounds and they are synthesized by condensation of phenols with naphthaldehydes.

Examples of the phenols used in the first invention are phenol and cresol, ethylphenol, propylphenol, butylphenol, amylphenol, hexylphenol, cyclohexylphenol, octylphenol, nonylphenol, xylenol, methylbutylphenol, chlorophenol, bromophenol, dichlorophenol and dibromophenol (including isomers thereof). These phenols may be used each alone or in combination of two or more.

Examples of the naphthaldehydes used in the first invention are naphthaldehyde, methylnaphthaldehyde, ethylnaphthaldehyde, methyl naphthyl ketone and methoxynaphthaldehyde (including isomers thereof). These naphthaldehydes may be used each alone or in combination of two or more.

Other aldehydes may be added to the above naphthaldehydes as far as the effects of the present invention are not damaged. As other aldehydes, mention may be made of, for example, formaldehyde, acetaldehyde, benzaldehyde, acrolein, crotonaldehyde, cinnamic aldehyde and glyoxal (including derivatives thereof).

The condensation reaction of phenols with naphthaldehydes can be carried out at 40°–150° C. in the presence of acid catalysts, for example, inorganic acids such as HCl and $H_2SO_4$, organic acids such as acetic acid, p-toluenesulfonic acid and thioglycollic acid, and Lewis acids or ion-exchange resins which show strong acidity, followed by known after-treatments such as washing with water and distilling off of unreacted phenols.

Furthermore, for imparting flame retardance to said polyhydric phenols, they may be substituted with halogens such as chlorine and bromine.

In this way, the polyhydric phenols represented by the formula (1) can be prepared.

In the compounds represented by the formula (1), the average recurring unit number n can be adjusted by the synthesis conditions such as molar ratio of the charged phenols and naphthaldehydes and amount of the catalysts. When n is 0, the melting point or melt viscosity of the condensates is the lowest and handling of the condensates is easy. But considering the balance of the properties of cured products of glycidyl ether compounds (epoxy resins) referred to hereinafter, the polyhydric phenols may be mixtures containing polyfunctional component in which n is more than 0 and in some uses, mixtures are rather preferred. Ordinarily, the number n can be in the range of about 0–10. For use as encapsulants, the average recurring unit number n is 0–5, preferably 0–3, more preferably 0–1.5 considering both the easiness in handling and the properties of cured products. When n exceeds 5, the softening point or melt viscosity of the desired products is high and this is not preferred for encapsulants. When the products are diluted with solvents for use, for example, as laminate sheets, the high melt viscosity is not necessarily disadvantageous for practical use and thus, the average recurring unit number n can be optionally adjusted depending on the objects.

The glycidyl ether compounds of the present invention can be obtained by the well known process which comprises glycidyl-etherifying the polyhydric phenols of the first invention. A typical process comprises reacting the polyhydric phenols with epihalohydrins such as epichlorohydrin in the presence of alkalis such as sodium hydroxide. Especially when products of high purity are desired, the reaction is preferably carried out in an aprotic solvent as described in Japanese Patent Kokai (Laid-Open) No. Sho 60-31517. The resulting glycidyl ether compounds can be used as epoxy resins.

The third invention relates to an epoxy resin composition comprising the above glycidyl ether compound and a curing agent.

Examples of the curing agent used in the third invention are polyhydric phenols such as phenol novolaks, amine curing agents such as dicyandiamide, diaminodiphenylmethane and diaminodiphenyl sulfone and acid anhydride curing agents such as pyromellitic anhydride, trimellitic anhydride and benzophenonetetracarboxylic acid. The polyhydric phenols are preferred.

Examples of the polyhydric phenols as curing agents are polycondensates of one or more phenols such as phenol, various alkylphenols and naphthols with aldehydes such as formaldehyde, acetaldehyde, acrolein, glyoxal, benzaldehyde, naphthaldehyde and hydroxybenzaldehyde or ketones such as cyclohexanone and acetophenone, vinyl polymerization type polyhydric phenols such as polyvinylphenol and polyisopropenylphenols, the polyhydric phenols of the present first invention, Friedel-Crafts type reaction products of phenols with diols such as those represented by the formula (3):

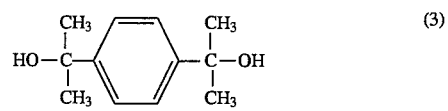

dialkoxy compounds represented by the following formula (4):

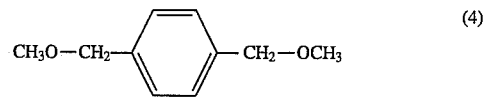

or, dihalogens represented by the following formula (5):

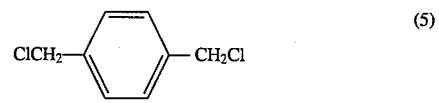

and Friedel-Crafts type reaction products of phenols with diolefins such as dicyclopentadiene and diisopropenylbenzene.

Amount of these curing agents used is 0.7–1.2 equivalent to epoxy group. When it is less than 0.7 equivalent or more than 1.2 equivalent to epoxy group, curing cannot be completed.

Furthermore, known additives such as fillers, curing accelerators, flame retardants, mold-releasing agents and surface treating agents can be added to the compositions depending on uses.

The fillers include, for example, silica, alumina, aluminum hydroxide, talc, clay and glass fibers. These fillers may be mixtures of those which are different in shape (sphere or fragment) or in size to increase filling amount.

The curing accelerators include, for example, imidazoles, tertiary amines and phosphorus compounds. The flame retardants include, for example, brominated epoxy resins and antimony trioxide.

The mold-releasing agents include, for example, waxes and metal salts of higher fatty acids such as zinc stearate. The surface treating agents include, for example, silane coupling agents.

Furthermore, various elastomers may be added to reduce the stress of cured products. Examples are addition type or reaction type elastomers such as polybutadienes, butadiene-acrylonitrile copolymers and silicone rubber.

Encapsulation of electronic parts such as semiconductors by the resin composition of the present invention can be performed by conventional methods such as transfer molding, compression molding and injection molding.

The fourth invention relates to an epoxy resin composition containing a specific polyhydric phenol as a curing agent.

Known epoxy resins may be used as those of component (a) in the composition of the fourth invention. Examples of the epoxy resins are novolak type epoxy resins which are reaction products of phenols such as phenol, alkylphenols, for example, o-cresol and naphthols with formaldehyde; glycidyl ether compounds derived from tri- or higher polyhydric phenols such as phloroglucin, tris-(4-hydroxyphenyl)-methane and 1,1,2,2-tetrakis(4-hydroxyphenyl)ethane; diglycidyl ether compounds derived from dihydric phenols such as bisphenol A, bisphenol F, tetramethylbiphenol, hydroquinone and resorcinol or halogenated bisphenols such as tetrabromobisphenol A; glycidyl ether compounds of polyhydric phenols obtained by condensation reaction of phenols with aromatic carbonyl compounds; glycidyl ether derived from hydrogenated bisphenol A; glycidyl amine compounds derived from p-aminophenol, m-aminophenol, 4-amino-m-cresol, 6-amino-m-cresol, 4,4'-diaminodiphenylmethane, 3,3'-diaminodiphenylmethane, 4,4'-diaminodiphenyl ether, 3,4'-diaminodiphenyl ether, 1,4-bis(4-aminophenoxy)benzene, 1,4-bis(3-aminophenoxy)-benzene, 1,3-bis(4-aminophenoxy)benzene, 1,3-bis(3-aminophenoxy)benzene, 2,2-bis(4-aminophenoxyphenyl)-propane, P-phenylenediamine, m-phenylenediamine, 2,4-toluenediamine, 2,6-toluenediamine, p-xylylenediamine, m-xylylenediamine, 1,4-cyclohexanebis(methylamine) and 1,3-cyclohexanebis(methylamine); glycidyl ester compounds derived from aromatic carboxylic acids such as p-oxybenzoic acid, m-oxybenzoic acid, terephthalic acid and isophthalic acid, hydantoin epoxy compounds derived from 5,5-dimethylhydantoin and the like, alicyclic epoxy resins such as 2,2-bis(3,4-epoxycyclohexyl)propane, 2,2-bis[4-(2,3-epoxypropoxy)cyclohexyl] propane, vinylcyclohexene dioxide, 3,4-epoxycyclohexylmethyl-3,4-epoxycyclohexane carboxylate, and N,N-diglycidylaniline. These epoxy resins are used each alone or in combination of two or more.

When bifunctional epoxy resins are used, it is preferred that polyhydric phenols used in combination with the epoxy resins have three or more functional groups. The composition comprising a bifunctional epoxy resin and a trifunctional or higher polyhydric phenol in combination is superior in curability when used as encapsulants. For these reasons and from the point of moisture resistance, novolak type epoxy resins such as o-cresol novolak and glycidyl ethers of polyhydric phenols obtained by condensation reaction of phenols and aromatic carbonyl compounds are preferred for use as encapsulants. Novolak type epoxy resins are more preferred.

As the phenols which are starting materials for the polyhydric phenols as component (b) used in the fourth invention, there may be used the phenols used in the first invention.

As the naphthaldehydes which are another starting materials for the polyhydric phenols used in the fourth invention, there may be used naphthaldehydes used in the first invention.

The condensation reaction of phenols and naphthaldehydes in the fourth invention can be carried out in the same manner as in the first invention.

The resulting condensates of phenols and naphthaldehydes can be represented by the formula (1).

The average recurring unit number can be adjusted by the synthesis conditions such as molar ratio of the phenols and naphthaldehydes to be charged and amount of the catalysts. When n is 0, the condensates have the lowest melting point and melt viscosity and can be easily handled, but considering the balance of the properties of cured products of glycidyl ether compounds (epoxy resins) referred to hereinafter, the polycondensates may be mixtures containing polyfunctional component in which n is more than 0 and in some uses, mixtures are rather preferred. Ordinarily, the number n can be in the range of about 0–10. For the use as encapsulants, the number n is 0–5, preferably 0–3, more preferably 0–1.5 considering both the easiness in handling and the properties of the cured products when used for encapsulants. When n exceeds 5, softening point or melt viscosity of the desired products is high and this is not preferred for use as encapsulants. When the products are diluted with solvents, for example, for use as laminate sheets, the high melt viscosity is not necessarily disadvantageous for practical use and thus, the number n can be optionally adjusted depending on the objects.

Moreover, the condensates which contain unreacted phenols can also be used as the polyhydric phenols used in the present invention and besides, they can contain unreacted phenols which are intentionally retained for adjustment of softening point or melt viscosity.

Furthermore, the composition of the fourth invention may contain a usual curing agent for epoxy resins in combination with the polyhydric phenols of the component (b). Examples of the curing agent are polyphenol compounds such as bisphenol A, tetrabromobisphenol A, bisphenol F, bisphenol S, bis(4-hydroxyphenyl)cyclohexane, bis(4-hydroxyphenyl)ethane, 1,3,3-trimethyl-1-m-hydroxyphenylindane-5 or 7-ol, 1,3,3-trimethyl-1-p-hydroxyphenylindane-6-ol, resorcinol, hydroquinone and catechol and phenol novolak resins which are reaction products of phenols such as phenol and o-cresol with formaldehyde, polycarboxylic acids such as maleic acid, phthalic acid, nadic acid, methyltetrahydrophthalic acid and methylnadic acid and anhydrides thereof, polyamine compounds such as diaminodiphenylmethane, diaminodiphenyl sulfone, diaminodiphenyl ether, phenylenediamine, diaminodicyclohexylmethane, xylylenediamine, toluenediamine and dichlorodiaminodiphenylmethane (including isomers thereof), ethylenediamine and hexamethylenediamine, and active hydrogen-containing compounds which are reactable with epoxy group such as dicyandiamide and tetramethylguanidine. Among them, the phenol novolak resins are preferred from the point of curability.

With reference to the proportion of the epoxy resin and the polyhydric phenol in the composition of the fourth invention, the amount of, the polyhydric phenol is preferably 0.7–1.2 equivalent weight per equivalent weight of the epoxy group. When it is less than 0.7 equivalent weight or more than 1.2 equivalent weight, curing is insufficient and low moisture absorption cannot be obtained.

Known curing accelerators may be used in curing of the resin composition of the fourth invention. Use of them is desirable especially for obtaining rapid curability in the use of the composition as encapsulants for semiconductors. Examples of the curing accelerators are organic phosphine compounds such as triphenylphosphine, tri-4-methylphenylphosphine, tri-4-methoxyphenylphosphine, tributylphosphine, trioctylphosphine and tri-2-cyanoethylphosphine, tertiary amines such as tributylamine, triethylamine and 1,8-diazabicyclo-(5,4,0)undecene-7 and triamylamine, quaternary ammonium salts such as benzyltrimethylammonium chloride, benzyltrimethylammonium hydroxide and triethylammonium tetraphenylborate, and imidazoles, but the curing accelerators are not limited to these examples. Among them, organic phosphines, 1,8-diazabicyclo(5,4,0)-undecene-7 and triethylammoniumtetraphenyl borate are preferred from the points of moisture resistance and curability and triphenylphosphine is especially preferred.

The resin composition of the present invention may contain inorganic fillers. As the fillers, mention may be made of silica, alumina, titanium white, aluminum hydroxide, talc, clay and glass fibers. Silica and alumina are especially preferred. The fillers may be mixtures of those of different shapes (sphere or fragment) or of different sizes to increase filling amount. Amount of the inorganic fillers when the composition is used for encapsulation of semiconductors is 25–90% by weight, preferably 60–85% by weight based on the total amount of the resin composition. When it is less than 25% by weight, the composition is inferior in moisture resistance and when it is more than 90% by weight, the composition has problems in moldability.

If necessary, the composition of the fourth invention may further contain one or more additives, e.g. mold-releasing agents such as natural waxes, synthetic waxes, higher fatty acids or metallic salts thereof and paraffins, colorants such as carbon black and surface treating agents such as silane coupling agents. Flame retardants such as antimony trioxide, phosphorus compounds and brominated epoxy resins may be added. Brominated epoxy resins are especially preferred for flame retardation.

Various elastomers may be added to the composition or may be previously reacted with the composition for reduction of stress. Examples of the elastomers are addition type or reaction type elastomers such as polybutadiene, butadiene-acrylonitrile copolymers, silicone rubbers and silicone oils.

In order to produce resin encapsulated type semiconductor devices by encapsulating electronic parts such as semiconductors using the resin composition of the fourth invention according to the fifth invention, the composition can be molded by known molding methods such as transfer molding, compression molding and injection molding.

As shown below, the polyhydric phenols of the first invention are used as starting materials for epoxy resins having low moisture absorption and high heat resistance.

The epoxy resins of the second invention which are glycidyl ethers of the condensates of phenols and naphthaldehydes and the compositions of the third invention can provide cured products lower in moisture absorption than those provided by conventional glycidyl ethers of o-cresol novolaks and furthermore can provide cured products lower in moisture absorption and higher in heat resistance than those provided by glycidyl ethers of tetramethylbiphenol which are known to be low moisture absorption resins. Therefore, the composition can be used in the wide variety of the fields such as adhesives, coatings, prepregs, laminate sheets, molding materials and casting materials.

Furthermore, the glycidyl ether compounds of the second invention are low in viscosity than glycidyl ethers of o-cresol novolak and when compositions are prepared with the glycidyl ether compounds, fillers can be used in a large amount and thus, the moisture absorption can be further lowered and the strength can be further increased and the compositions are useful as resin compositions for obtaining surface mounting.

The epoxy resin compositions of the fourth invention have low moisture absorption and are well balanced in heat resistance, hot toughness and adhesion as encapsulants for electronic parts. Moreover, the resin encapsulated type semiconductor devices of the fifth invention made using the above epoxy resins are superior in solder crack resistance.

The present invention is illustrated by way of the following Examples, but not limited thereby.

First, Examples of the first to third inventions will be given.

In the Examples, the "epoxy equivalent weight" is defined as the molecular weight of epoxy resin per one epoxy group. Furthermore, the "hydrolyzable chlorine content" means chlorine ion which is released when an epoxy resin is dissolved in dioxane, an alcoholic potassium hydroxide solution is added thereto and the mixture is heated for 30 minutes under refluxing and which is expressed by concentration in parts per million compound obtained by subjecting the chlorine ion to back titration with aqueous silver nitrate solution.

The cured moldings were evaluated in the following manners.

Glass transition temperature: This was measured using a thermo-mechanical analyzing instrument (SHIMADZU DT-30).

Flexural strength and flexural modulus: This was measured in accordance with JIS K-6911 using an Instron universal testing machine (SHIMADZU IS-10T).

Water absorption (index for moisture absorption): Change in weight was measured using a thermohygrostat (TABAI PR-2) under the conditions of 85° C./85%RH.

Spiral flow: This was measured in accordance with EMMI-1-66 under the conditions of 175° C. and 70 kg/cm$^2$.

Preparation of condensates of phenols and naphthaldehydes and glycidyl-etherification of the condensates.

EXAMPLE 1

244.4 g (2.00 mol) of 2,6-xylenol, 78.1 g (0.50 mol) of 1-naphthaldehyde, 225.8 g of toluene and 9.5 g of p-toluenesulfonic acid monohydrate were charged in a 1 liter four-necked flask provided with a stirrer, a thermometer and a condenser attaching a water separator and stirred to perform dissolution.

The inner temperature was elevated to a refluxing temperature of 130° C. and water produced by the reaction was distilled off from the reaction system by the water separator. The reaction was carried out at 130° C. for 7 hours.

After completion of the reaction, 258 g of toluene was added to the reaction mixture, followed by neutralization with aqueous sodium hydrogencarbonate solution and separation into layers and thereafter repeating washing with water and separation into layers. The toluene layer was dried and thereafter, toluene and 2,6-xylenol were distilled off by a rotary evaporator to obtain 193.5 g of a condensate of 2,6-xylenol and 1-naphthaldehyde. The resulting condensate had a molecular weight of 382 measured by FD-MASS spectrum and a melting point of 95°–105° C.

100.0 g of the resulting condensate of 2,6-xylenol and 1-naphthaldehyde was charged in a reactor provided with a thermometer, a stirrer, a dropping funnel and a condenser attaching a water separator and dissolved in 343.2 g of epichlorohydrin and 171.6 g of dimethyl sulfoxide. With keeping the pressure in the reaction system at 41 Torr, 43.6 g of 48.6% aqueous sodium hydroxide solution was continuously dropped to the solution at 48° C. over a period of 1.5 hour, during which reaction was carried out with cooling and liquefying the co-boiling epichlorohydrin and water and returning the organic layer to the reaction system keeping the temperature at 48° C.

After completion of the reaction, unreacted epichlorohydrin was removed by concentration under reduced pressure and the glycidyl ether compound containing by-product salts and dimethyl sulfoxide were dissolved in methyl isobutyl ketone, and the by-product salts and the dimethyl sulfoxide were removed by washing with water.

Epoxy equivalent weight and hydrolyzable chlorine content of the thus obtained glycidyl ether compound were 258 g/eq and 260 ppm, respectively.

EXAMPLE 2

Reaction was carried out in the same manner as in Example 1 except that 81.1 g (0.75 mol) of o-cresol was used in place of 2,6-xylenol and 1-naphthaldehyde was charged in an amount of 78.1 g (0.50 mol), thereby to obtain 137.7 g of a condensate of o-cresol and 1-naphthaldehyde. Fragments of 354, 600, 846, 1092, 1338 and 1584 were detected in FD-MASS spectrum of the condensate. The average recurring unit number n obtained by GPC was 1.61. In the same manner as in Example 1, 123.6 g of the resulting condensate of o-cresol and 1-naphthaldehyde was charged in a reactor provided with a thermometer, a stirrer, a dropping funnel and a condenser attaching a water separator and dissolved in 389.4 g of epichlorohydrin and 194.7 g of dimethyl sulfoxide. With keeping the pressure in the reaction system at 41 Torr, 37.5 g of 48.6% aqueous sodium hydroxide solution was continuously dropped to the solution at 48° C. over a period of 1.5 hour, during which reaction was carried out with cooling and liquefying the co-boiling epichlorohydrin and water and returning the organic layer to the reaction system keeping the temperature at 48° C., followed by subjecting to after-treatments to obtain the desired glycidyl ether compound.

Epoxy equivalent weight and hydrolyzable chlorine content of the thus obtained glycidyl ether compound were 302 g/eq and 260 ppm, respectively.

EXAMPLE 3

Reaction was carried out in the same manner as in Example 2 except that o-cresol was charged in an amount of 378.4 g (3.50 mol) and 1-naphthaldehyde was charged in an amount of 109.3 g (0.70 mol), thereby to obtain 230.2 g of a condensate of o-cresol and 1-naphthaldehyde. Fragments of 354 and 600 were detected in FD-MASS spectrum of the condensate. The average recurring unit number n obtained by GPC was 0.24. In the same manner as in Example 1, 146.4 g of the resulting condensate of o-cresol and 1-naphthaldehyde was charged in a reactor provided with a thermometer, a stirrer, a dropping funnel and a condenser attaching a water separator and dissolved in 518.0 g of epichlorohydrin and 259.0 g of dimethyl sulfoxide. With keeping the pressure in the reaction system at 41 Torr, 62.5 g of 48.6% aqueous sodium hydroxide solution was continuously dropped to the solution at 48° C. over a period of 1.5 hour, during which reaction was carried out with cooling and liquefying the co-boiling epichlorohydrin and water and returning the organic layer to the reaction system keeping the temperature at 48° C., followed by subjecting to after-treatments to obtain the desired product.

Epoxy equivalent weight and hydrolyzable chlorine content of the thus obtained glycidyl ether compound were 279 g/eq and 220 ppm, respectively.

EXAMPLE 4

Reaction was carried out in the same manner as in Example 1 except that 100.0 g (0.61 mol) of 2-t-butyl-4-methyl-phenol was charged in place of 2,6-xylenol and 1-naphthaldehyde was charged in an amount of 47.5 g (0.30 mol). After toluene was distilled off, the precipitated crystal was washed and dried to obtain 137.3 g of a condensate of 2-t-butyl-4-methyl-phenol and 1naphthaldehyde. Molecular weight of the condensate according to FD-MASS spectrum was 466. In the same manner as in Example 1, 100.3 g of the resulting condensate was charged in a reactor provided with a thermometer, a stirrer, a dropping funnel and a condenser attaching a water separator and dissolved in 278.4 g of epichlorohydrin and 139.2 g of dimethyl sulfoxide. With keeping the pressure in the reaction system at 41 Torr, 35.4 g of 48.6% aqueous sodium hydroxide solution was continuously dropped to the solution at 48° C. over a period of 1.5 hour, during which reaction was carried out with cooling and liquefying the co-boiling epichlorohydrin and water and returning the organic layer to the reaction system keeping the temperature at 48° C., followed by subjecting to after-treatments to obtain the desired glycidyl ether compound.

Epoxy equivalent weight and hydrolyzable chlorine content of the thus obtained glycidyl ether compound were 339 g/eq and 268 ppm, respectively.

COMPARATIVE EXAMPLE 1

500 g of 2,6-xylenol was treated in the same manner as in Example 1 of Japanese Patent Kokai (Laid Open) No. Hei 1-283241 to obtain 3,3',5,5'-tetramethylbiphenol.

Then, 100 g of the resulting 3,3',5,5'-tetramethylbiphenol was charged in a reactor provided with a thermometer, a stirrer, a dropping funnel and a condenser attaching a water separator and dissolved in 535.0 g of epichlorohydrin and 267.0 g of dimethyl sulfoxide. With keeping the pressure in the reaction system at 41 Torr, 48.6% aqueous sodium hydroxide solution was continuously dropped to the solution at 48° C. over a period of 5 hours.

Thereafter, treatments were carried out in the same manner as in Example 1 to obtain the glycidyl ether compound. Epoxy equivalent weight and hydrolyzable chlorine content of the thus obtained glycidyl ether compound were 194 g/eq and 220 ppm, respectively.

COMPARATIVE EXAMPLE 2

A glycidyl ether compound of o-cresol novolak (Sumi-epoxy ESCN-195, a trade name, manufactured by sumitomo Chemical Co., Ltd.) was used as a conventional glycidyl ether compound.

COMPARATIVE EXAMPLE 3

A glycidyl ether compound of bisphenol A (Sumiepoxy ELA-070, a trade name, manufactured by Sumitomo Chemical Co., Ltd.) was used as a conventional glycidyl ether compound.

Evaluation of the epoxy resin compositions Examples 5–8 and

COMPARATIVE EXAMPLES 4–6

Cured moldings of the glycidyl ether compounds (epoxy resins) prepared in Examples 1–4 and Comparative Examples 1–3 were evaluated. To each of the epoxy resins were added a phenol novolak (Tamanol 759 manufactured by Arakawa Chemical Co., Ltd.) as a curing agent, triphenylphosphine as a curing accelerator, a fused silica (FS-891 manufactured by Denki Kagaku Kogyo K.K.) as a filler, carnauba wax as a releasing agent and a coupling agent (SH-6040 manufactured by Toray Dow-Corning Co.) in the amounts (g) as shown in Table 1. The mixture was kneaded with heating by a roll of 110° C./50° C. and transfer molded under the conditions of 175° C./70 kg/cm$^2$/90 sec.

The molding was further subjected to postcuring in an oven at 180° C. for 5 hours to obtain a cured molding.

Glass transition temperature, water absorption, flexural strength and flexural modulus of the cured molding were measured and the results are shown in Table 2.

Next, Examples of the fourth and fifth invention are shown below.

In these Examples, the "hydroxyl equivalent weight" is defined to be molecular weight of resin per one hydroxyl group. The average recurring unit number n was obtained from GPC (TRIROTOR SR-II manufactured by Nihon Bunko Kogyo Co.).

Kneaded products and cured moldings were evaluated as follows.

Gel time: 0.5 g of each of the kneaded products obtained in Examples and Comparative Examples was put in a dent portion of a hot plate at 180° C. and the time required for gelation was measured.

Glass transition temperature: This was measured using a thermo-mechanical analytical instrument (SHIMADZU DT-30).

Barcol hardness: This was measured in accordance with ASTM D-648 by Model 935 under the conditions of 175° C./2 min.

Hot flexural strength, hot flexural modulus and hot flexural strain (index for toughness): These were measured in accordance with JIS K-6911 using Instron universal testing machine (SHIMADZU IS-10T) at 240° C. The hot flexural strain was calculated from the following formula.

Hot flexural strain=6×thickness of sample×maximum amount of deflection/(distance between the supports)$^2$
(The origin: "Handbook for Plastic Tests")

TABLE 1

| | Example 5 | Example 6 | Example 7 | Example 8 | Comparative Example 4 | Comparative Example 5 | Comparative Example 6 (unit: g) |
|---|---|---|---|---|---|---|---|
| Glycidyl ether | Example 1 100 | Example 2 100 | Example 3 100 | Example 4 100 | Comparative Example 1 100 | Comparative Example 2 100 | Comparative Example 3 100 |
| Phenol-novolak | 42.9 | 36.4 | 39.1 | 32.2 | 56.7 | 56.0 | 61.8 |
| Triphenyl-phosphine | 1.5 | 1.5 | 1.5 | 1.5 | 1.5 | 1.5 | 1.5 |
| Filler | 333 | 318 | 325 | 309 | 366 | 364 | 378 |
| Releasing agent | 1.5 | 1.5 | 1.5 | 1.5 | 1.5 | 1.5 | 1.5 |
| Coupling agent | 2.0 | 2.0 | 2.0 | 2.0 | 2.0 | 2.0 | 2.0 |

TABLE 2

| | | Example 5 | Example 6 | Example 7 | Example 8 | Comparative Example 4 | Comparative Example 5 | Comparative Example 6 |
|---|---|---|---|---|---|---|---|---|
| Flow (inch) | | 86.5 | 40.9 | 78.0 | 65.9 | 48.2 | 52.5 | 69.6 |
| Glass transition temperature (°C.) | | 153 | 170 | 159 | 143 | 130 | 163 | 128 |
| Flexural strength (kg/mm$^2$) | | 12.3 | 13.0 | 13.4 | 12.4 | 14 | 13 | 13 |
| Flexural modulus (kg/m$^2$) | | 1400 | 1320 | 1380 | 1350 | 1360 | 1350 | 1310 |
| Water absorption % | 24 hr | 0.18 | 0.19 | 0.16 | 0.12 | 0.20 | 0.25 | 0.24 |
| | 72 hr | 0.29 | 0.30 | 0.26 | 0.21 | 0.33 | 0.37 | 0.38 |

Water absorption: Change in weight of sample was measured using a thermo-hygrostat (TABAI PR-2) under the conditions of 85° C./85%RH.

Spiral flow: This was measured in accordance with EMMI-1-66 under the conditions of 175° C. and 70 kg/cm$^2$.

Adhesion: A kneaded product was transfer molded on an aluminum foil and the adhesion was evaluated by peel strength of the foil.

Solder crack resistance: Test IC (52 pin QFP packages: thickness of package 2.05 mm) were allowed to absorb moisture under the conditions of 85° C./85%RH/72 hr and immediately thereafter, dipped in a bath of solder at 240° C. for 30 seconds. The solder crack resistance was evaluated by the number of IC in which cracks occurred after the dipping. The number of the test IC was 10.

PREPARATION OF POLYHYDRIC PHENOLS

PREPARATION EXAMPLE 1

405.8 g (3.75 mol) of m-cresol, 78.1 g (0.50 mol) of 1-naphthaldehyde, 341 g of toluene and 1.33 g of p-toluenesulfonic acid monohydrate were charged in a four-necked flask provided with a stirrer, a thermometer and a condenser attaching a water separator and stirred to perform dissolution.

The inner temperature was elevated to a refluxing temperature of 130° C. and water produced by the reaction was distilled off from the reaction system by the water separator. The reaction was carried out at 130° C. for 4 hours.

After completion of the reaction, the reaction mixture was neutralized with aqueous sodium hydroxide solution and 600 g of methyl isobutyl ketone was added thereto, followed by repeating washing with water and separation into layers. Then, the organic layer was concentrated by a rotary evaporator to obtain 168.2 g of the desired polyhydric phenol (hereinafter referred to as "MCNAN"). Softening point of the product was 117.5° C., hydroxyl group equivalent was 183 g/eq and n was 0.31.

PREPARATION EXAMPLE 2

Reaction was carried out in the same manner as in Preparation Example 1 except that 405.8 g (3.75 mol) of o-cresol was charged in place of m-cresol, 1-naphthaldehyde was charged in an amount of 78.1 g (0.50 mol) and p-toluenesulfonic acid monohydrate was charged in an amount of 0.95 g, thereby to obtain 170.0 g of the desired polyhydric phenol (hereinafter referred to as "OCNAN"). Fragments of 354, 600, 846, 1092, 1338 and 1584 were detected in FD-MASS spectrum of the product. Softening point of the product was 111° C., hydroxyl equivalent weight was 181 g/eq and n was 0.14.

PREPARATION EXAMPLE 3

160.8 g (0.6 mol) of bisphenol cyclohexane (Antigen W manufactured by Sumitomo Chemical Co., Ltd.), 28.1 g (0.18 mol) of 1-naphthaldehyde, 241.2 g of isoamyl alcohol and 3.42 g of p-toluenesulfonic acid monohydrate were charged in a 1 liter four-necked flask provided with a stirrer, a thermometer and a condenser attaching a water separator and stirred to perform dissolution.

The inner temperature was elevated to a refluxing temperature of 80° C. under a reduced pressure of 70 Torr and water produced by the reaction was distilled off from the reaction system by the water separator. The reaction was carried out at 80° C. for 6 hours.

After completion of the reaction, the reaction mixture was neutralized with aqueous sodium hydroxide solution and separated into layers, followed by repeating washing with water and separation into layers. Then, the organic layer was concentrated by a rotary evaporator to obtain 181.7 g of the desired polyhydric phenol (hereinafter referred to as "PHCHNA"). Hydroxyl group equivalent of the product was 154 g/eq, softening point was 110° C. and n was 0.75.

EXAMPLES 9–14

Each of the polyhydric phenols obtained in the above Preparation Examples 1–3 as a curing agent, a glycidyl ether of o-cresol novolak (Sumi-epoxy ESCN-195, a trade name, manufactured by Sumitomo Chemical Co., Ltd.; epoxy equivalent weight: 201 g/eq and hydrolyzable chlorine content: 330 ppm) and a glycidyl ether of a polyphenol obtained by condensation of a phenol and hydroxybenzaldehyde (hereinafter referred to as "PHG") (epoxy equivalent weight: 213 g/eq and hydrolyzable chlorine content: 200 ppm) as epoxy resins, triphenylphosphine as a curing accelerator, a fused silica (FS-891 manufactured by Denki Kagaku Kogyo K.K.) as a filler, carnauba wax as a releasing agent and a coupling agent (SH-6040 manufactured by Toray Dow-Corning Co.) were blended in the amounts (g) as shown in Table 3. The mixture was kneaded with heating by a roll and transfer molded (curing time 90 seconds).

The molding was further subjected to postcuring in an oven at 180° C. for 5 hours to obtain a cured molding.

COMPARATIVE EXAMPLES 7–8

Cured moldings were obtained in the same manner as in the above Examples except that a phenol novolak (Tamanol 759 manufactured by Arakawa Chemical Co., Ltd., hydroxyl group equivalent: 110 g/eq). Blending ratios are shown in Table 3.

Gel time, spiral flow, Barcol hardness, glass transition temperature, water absorption, hot flexural strength, hot flexural modulus, hot flexural strain, adhesion and solder crack resistance of the cured moldings obtained in the Examples and Comparative Examples were measured. The results are shown in Table 4.

TABLE 3

(unit: part by weight)

| | Example | | | | | | Comparative Example | |
|---|---|---|---|---|---|---|---|---|
| | 9 | 10 | 11 | 12 | 13 | 14 | 7 | 8 |
| ESCN-195XL | 100 | 100 | 100 | — | — | — | 100 | — |
| PHG | — | — | — | 100 | 100 | 100 | — | 100 |
| MCNAN | 93.2 | — | — | 85.9 | — | — | — | — |

TABLE 3-continued (unit: part by weight)

| | Example | | | | | | Comparative Example | |
|---|---|---|---|---|---|---|---|---|
| | 9 | 10 | 11 | 12 | 13 | 14 | 7 | 8 |
| OCNAN | — | 92.2 | — | — | 85.0 | — | — | — |
| PHCHNA | — | — | 78.6 | — | — | 72.3 | — | — |
| NANAN | — | — | — | — | — | — | — | — |
| Phenol novolak | — | — | — | — | — | — | 56.0 | 51.6 |
| Triphenyl-phosphine | 1.5 | 1.5 | 1.5 | 1.5 | 1.5 | 1.5 | 1.5 | 1.5 |
| Filler | 450.8 | 448.5 | 416.7 | 433.0 | 431.7 | 402.0 | 364.0 | 353.7 |
| Releasing agent | 1.5 | 1.5 | 1.5 | 1.5 | 1.5 | 1.5 | 1.5 | 1.5 |
| Coupling agent | 2.0 | 2.0 | 2.0 | 2.0 | 2.0 | 2.0 | 2.0 | 2.0 |

TABLE 4

| | Example | | | | | | Comparative Example | |
|---|---|---|---|---|---|---|---|---|
| | 9 | 10 | 11 | 12 | 13 | 14 | 7 | 8 |
| Gel time (sec) | 48 | 40 | 36 | 38 | 37 | 34 | 33 | 36 |
| Spiral flow (inch) | 50 | 47 | 52 | 40 | 39 | 45 | 44 | 49 |
| Barcol Hardness (Barcol 935) | 35 | 40 | 50 | 35 | 37 | 55 | 78 | 82 |
| Glass transition temperature (°C.) | 165 | 163 | 168 | 189 | 169 | 175 | 155 | 185 |
| Hot flexural strength (kg/mm$^2$) | 0.30 | 0.31 | 0.35 | 0.31 | 0.34 | 0.40 | 0.90 | 1.0 |
| Hot flexural modulus (kg/mm$^2$) | 12.2 | 12.0 | 20.0 | 10.0 | 11.0 | 33.2 | 86.7 | 69.2 |
| Hot flexural strain (mm/mm) | 0.0237 | 0.0232 | 0.0175 | 0.0569 | 0.0916 | 0.0172 | 0.0100 | 0.0132 |
| Adhesion (g/cm) | 310 | 330 | 380 | 350 | 410 | 410 | 300 | 200 |
| Water absorption (%) 24 hr | 0.177 | 0.155 | 0.165 | 0.230 | 0.215 | 0.221 | 0.217 | 0.365 |
| 48 hr | 0.239 | 0.213 | 0.230 | 0.280 | 0.273 | 0.278 | 0.302 | 0.449 |
| 72 hr | 0.278 | 0.257 | 0.270 | 0.303 | 0.301 | 0.308 | 0.364 | 0.488 |
| Solder crack resistance | 1 | 1 | 1 | 0 | 1 | 0 | 10 | 5 |

What is claimed is:

1. An epoxy resin composition which comprises a curable glycidyl ether compound represented by the formula:

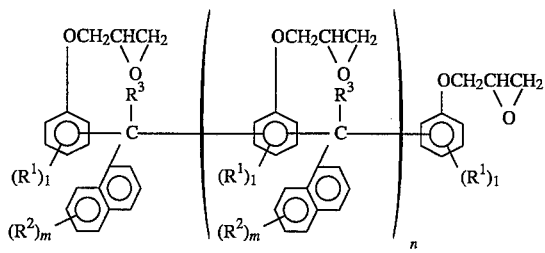

wherein $R^1$ independently represents a halogen atom, an alkyl or cycloalkyl group having up to 9 carbon atoms, an alkoxy group having 4 or less carbon atoms or an aryl group and may be identical or different when l is 2 or more; $R^2$ independently represents a halogen atom, an alkoxy group having 4 or less carbon atoms or an alkyl group having 6 or less carbon atoms and may be identical or different when m is 2 or more; $R^3$ independently represents a hydrogen atom or an alkyl group having 6 or less carbon atoms; the average recurring unit member n is 0–10; l is 0–4; and m is 0–7, and a polyhydric phenol as a curing agent.

2. An epoxy resin composition according to claim 1, wherein the polyhydric phenol is a phenol novolak.

3. An epoxy resin composition according to claim 1, wherein the average recurring unit number n in the formula of the glycidyl ether compound is 0 to 5.

4. An epoxy resin composition according to claim 1, wherein the average recurring unit number n in the formula of the glycidyl ether compound is 0 to 3.

5. An epoxy resin composition according to claim 1, which further comprises an inorganic filler.

6. An epoxy resin composition according to claim 5, wherein the inorganic filler is at least one member selected from the group consisting of silica, alumina, titanium white, aluminum hydroxide, talc, clay and glass fibers.

7. An encapsulating process comprising encapsulating a semiconductor device with an epoxy resin composition according to claim 1.

8. An epoxy resin composition which comprises a curable glycidyl ether compound represented by the formula:

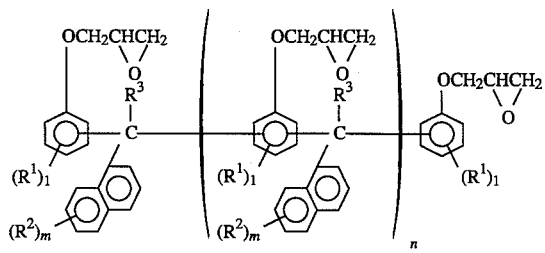

wherein $R^1$ independently represents a halogen atom, an alkyl or cycloalkyl group having up to 9 carbon atoms, an alkoxy group having 4 or less carbon atoms or an aryl group and may be identical or different when l is 2 or more; $R^2$ independently represents a halogen atom, an alkoxy group having 4 or less carbon atoms or an alkyl group having 6 or less carbon atoms and may be identical or different when m is 2 or more; $R^3$ independently represents a hydrogen atom or an alkyl group having 6 or less carbon atoms; the average recurring unit member n is 0–10; l is 0–4; and m is 0–7;

an effective amount of a curing agent, wherein said curing agent is a phenol novolak; and at least one inorganic filler.

9. An encapsulating process comprising encapsulating a semiconductor device with an epoxy resin composition according to claim 8.

* * * * *